US00PP36977P2

(12) United States Plant Patent
Halladin

(10) Patent No.: US PP36,977 P2
(45) Date of Patent: Sep. 23, 2025

(54) JAPANESE MAPLE TREE NAMED 'INWQ-E92'

(50) Latin Name: ***Acer pseudosieboldianum* x *palmatum***
Varietal Denomination: INWQ-E92

(71) Applicant: Early Morning LLC, Greendale, IN (US)

(72) Inventor: Paul H. Halladin, Boring, OR (US)

(73) Assignee: EARLY MORNING LLC, Greendale, IN (US)

( * ) Notice: Subject to any disclaimer, the term of this patent is extended or adjusted under 35 U.S.C. 154(b) by 0 days.

(21) Appl. No.: 18/895,045

(22) Filed: Sep. 24, 2024

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./224
See application file for complete search history.

*Primary Examiner* — Shubo Zhou
*Assistant Examiner* — Zachariah Allan Kay
(74) *Attorney, Agent, or Firm* — Weatherly IP Solutions, LLC; James Weatherly

(57) ABSTRACT

A new and distinct variety of Japanese maple tree having a small to moderate-size with red-lace leaves that turn greyish red with maturity, that is hardy in USDA Zones 4 to 8, with an arching, cascading branching and a moderate growth rate with a mushroom-like habit, is disclosed.

5 Drawing Sheets

Genus and species: *Acer pseudosieboldianum* x *palmatum.*

Denomination: 'INWQ-E92'.

BACKGROUND

'INWQ-E92' is a new and distinct variety of Japanese maple. It is a new hardy red lace-leaf Japanese maple tree for USDA Zones 4-8, the result of extensive breeding, selecting, screening and testing. 'INWQ-E92' originated from a tree breeding program focused on expanding the range of Japanese maples to include northern cold regions, including USDA Zone 4. For cold hardiness, the genetics from *Acer pseudosieboldianum* (USDA Zone 4) have been combined with the refined, yet less cold-tolerant genetics of *Acer palmatum*. (USDA Zone 5 or 6).

The general term "Japanese maples" applies to species, forms, and cultivars within Section and Series Palmata including native Japanese species *Acer palmatum, japonicum, shirasawanum*, and *sieboldiamim* and two not native species, the West Coast North American species *Acer circinatum* or Vine maple and *Acer pseudosieboldianum* or Korean maple.

*Acer pseudosieboldianum* is the foundation breeding genetics used for enhancing hardiness. This species is native from the Korean peninsula north into the biodiverse forested Ussuri river region of Eastern China and Russia, a region spared from past glaciation enabling long periods of uninterrupted species development from a former warm climate to the current cold dry winter climate. *Acer pseudosieboldianum* successfully grows in the Upper Midwest region of USDA zone 4 with some seedling and cultivar success in USDA zone 3. Besides hardiness, Korean maple has features of sun tolerant vibrant green summer foliage, outstanding multicolored fall foliage, but as a garden tree the typically marcescent leaves and coarse, open, erratic branching and unpredictable habit is a detraction.

The species native to Japan: *Acer palmatum, japonicum, shirasawanum*, and *sieboldianum* have long been garden worthy trees with hundreds of years of human selection and refinement. These species and selected cultivars are USDA Zone 5 or 6 or 7 and as such are either marginal or not hardy as garden trees for much of North America hence the breeding program combination of garden qualities genetics crossed with hardy genetics.

'INWQ-E92' originated from an open-pollination between an unnamed and unpatented female F2 hybrid *Acer pseudosieboldianum* x *palmatum* with an unknown male *Acer pseudosieboldianum* x *palmatum* in Spring 2011 in Boring, Oregon. Seeds from the open-pollination were collected and planted in April 2012 and germinated in June 2012. 'INWQ-E92' was first identified as a superior seedling in September 2015 in Boring, Oregon from the seedlings of the initial cross.

'INWQ-E92' was first propagated by grafting in August 2018 onto *Acer palmatum* seedling rootstock. 'INWQ-E92' reproduces true to type in successive generations of asexual reproduction via grafting

SUMMARY

The following are the most outstanding and distinguishing characteristics of this new variety when grown under normal horticultural practices in Boring, Oregon.

1. A small to moderate-sized Japanese maple tree with red-lace leaves that turn a dark greyish-red with maturity;
2. Hardy in USDA Zones 4 to 8;
3. Arching and cascading branching; and
4. Moderate growth with a mushroom-like habit.

DESCRIPTION OF THE PHOTOGRAPHS

This new Japanese maple tree is illustrated by the accompanying photographs which show the plant's overall plant habit including form, leaves and seed. The photographs were taken outdoors in Boring, Oregon between June 2023 and September 2024. The colors shown are as true as can be reasonably obtained by conventional photographic procedures.

DETAILED DESCRIPTION

Figure 1:
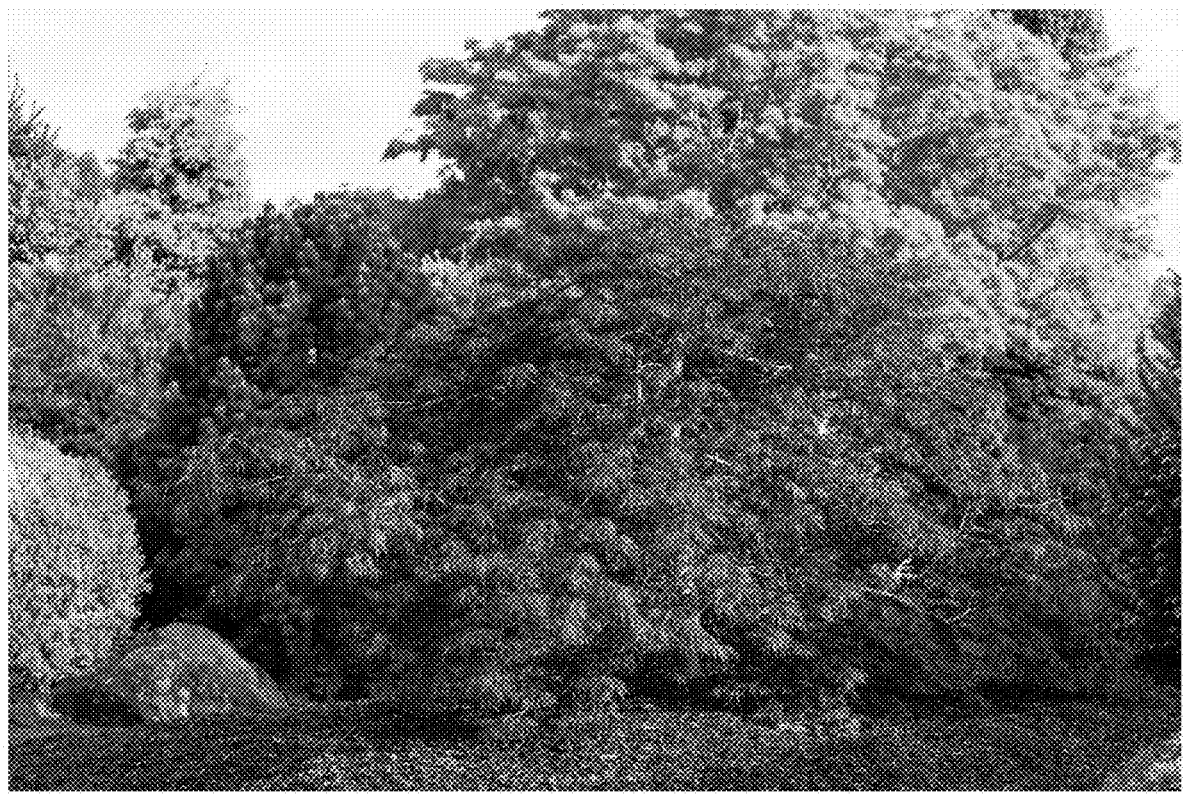
FIG. 1 shows a 12-year-old tree of 'INWQ-E92' in the foreground.
Figure 2:
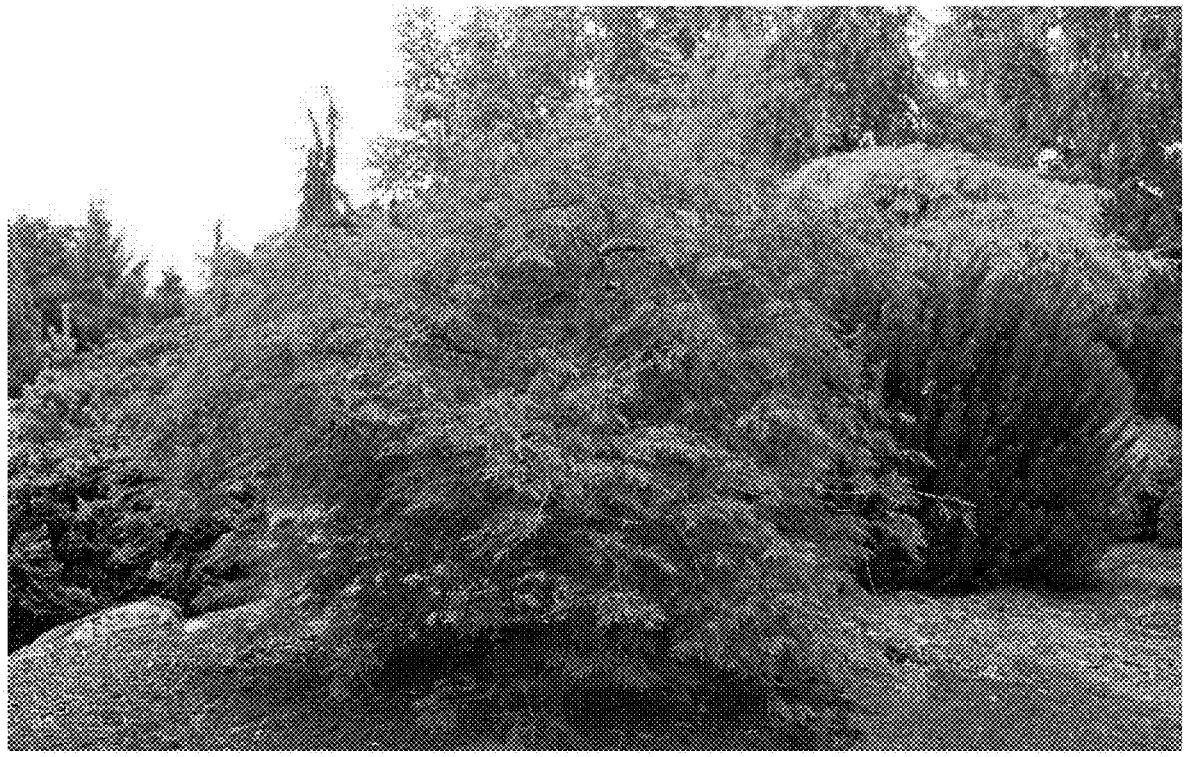
FIG. 2 shows an 11-year-old tree of 'INWQ-E92' in the foreground.
Figure 3:
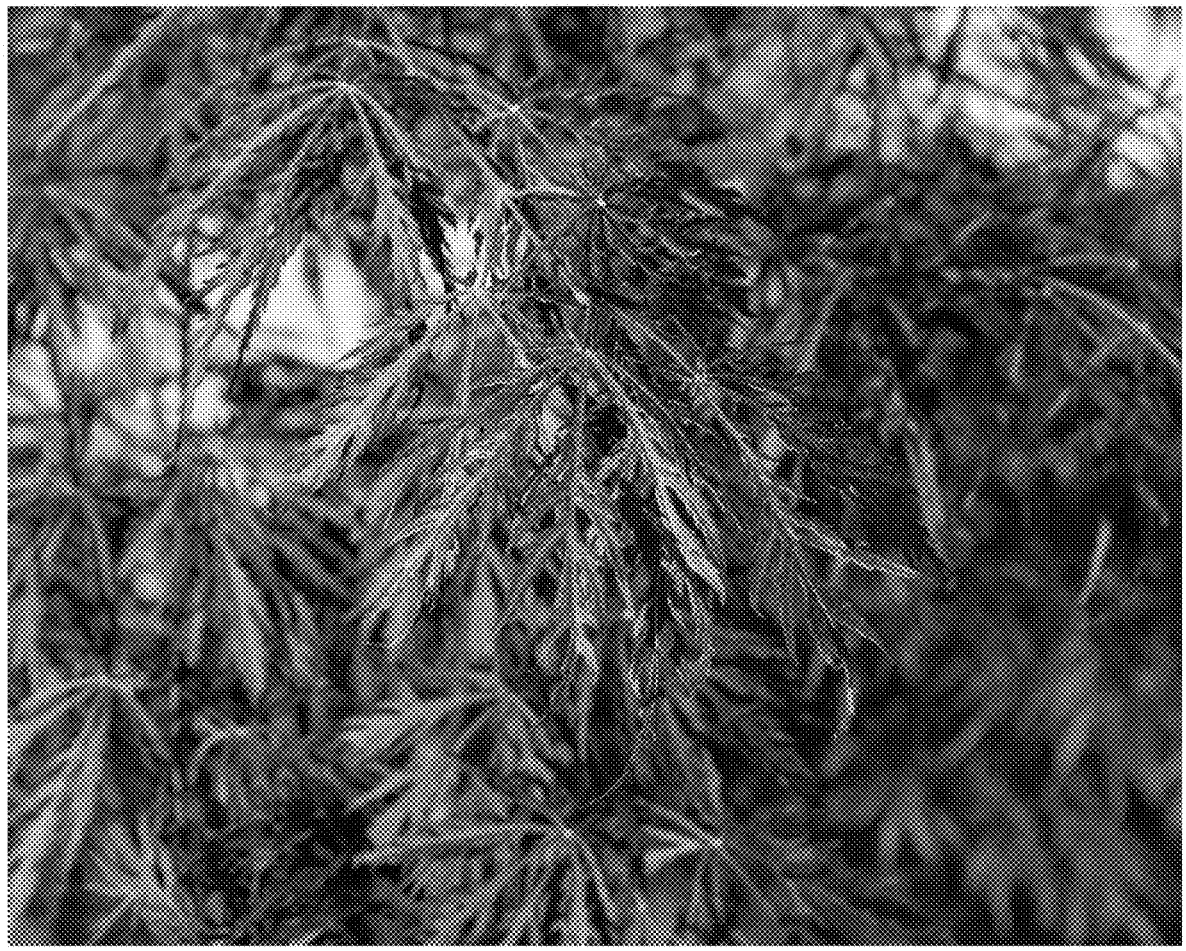
FIG. 3 shows a close-up of the immature spring foliage of a 5-year-old 'INWQ-E92' tree and the pubescence on the foliage.
Figure 4:
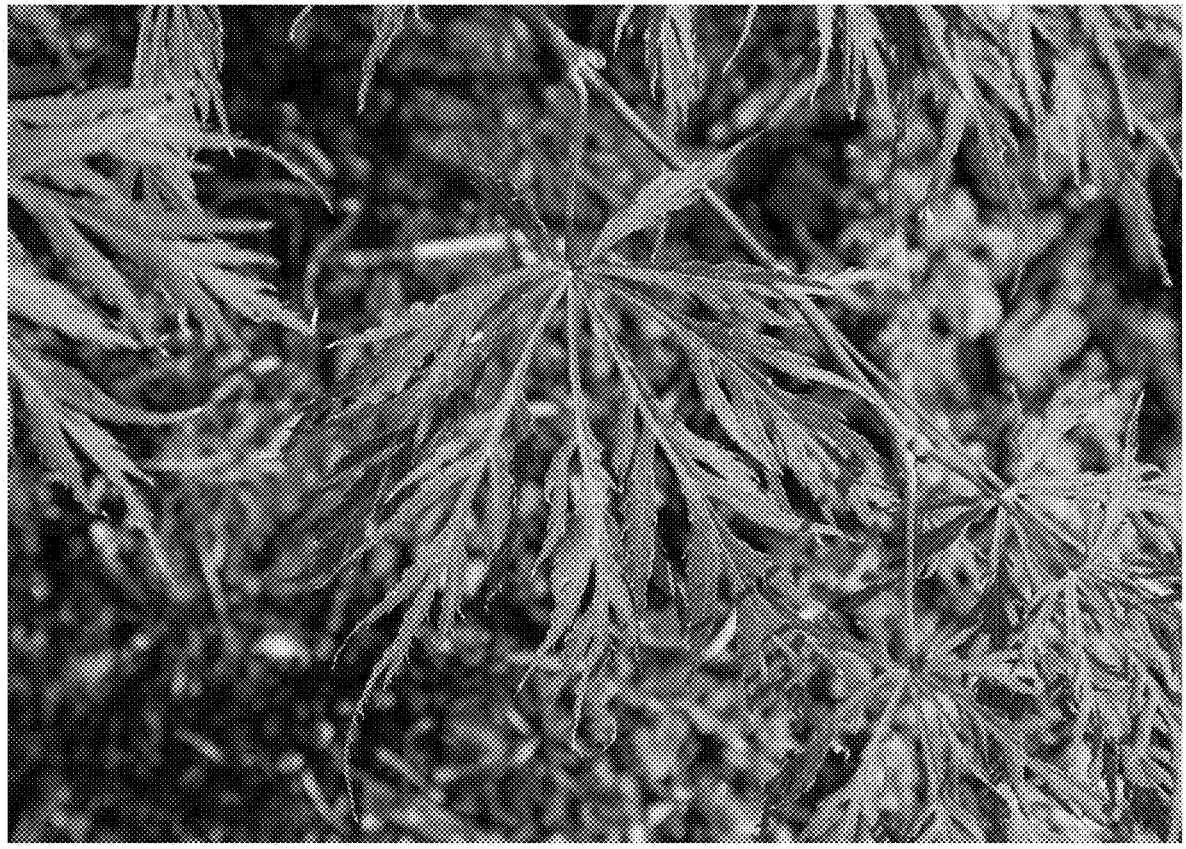
FIG. 4 shows a close-up of the mature foliage of a 12-year-old 'INWQ-E92' tree.
Figure 5:
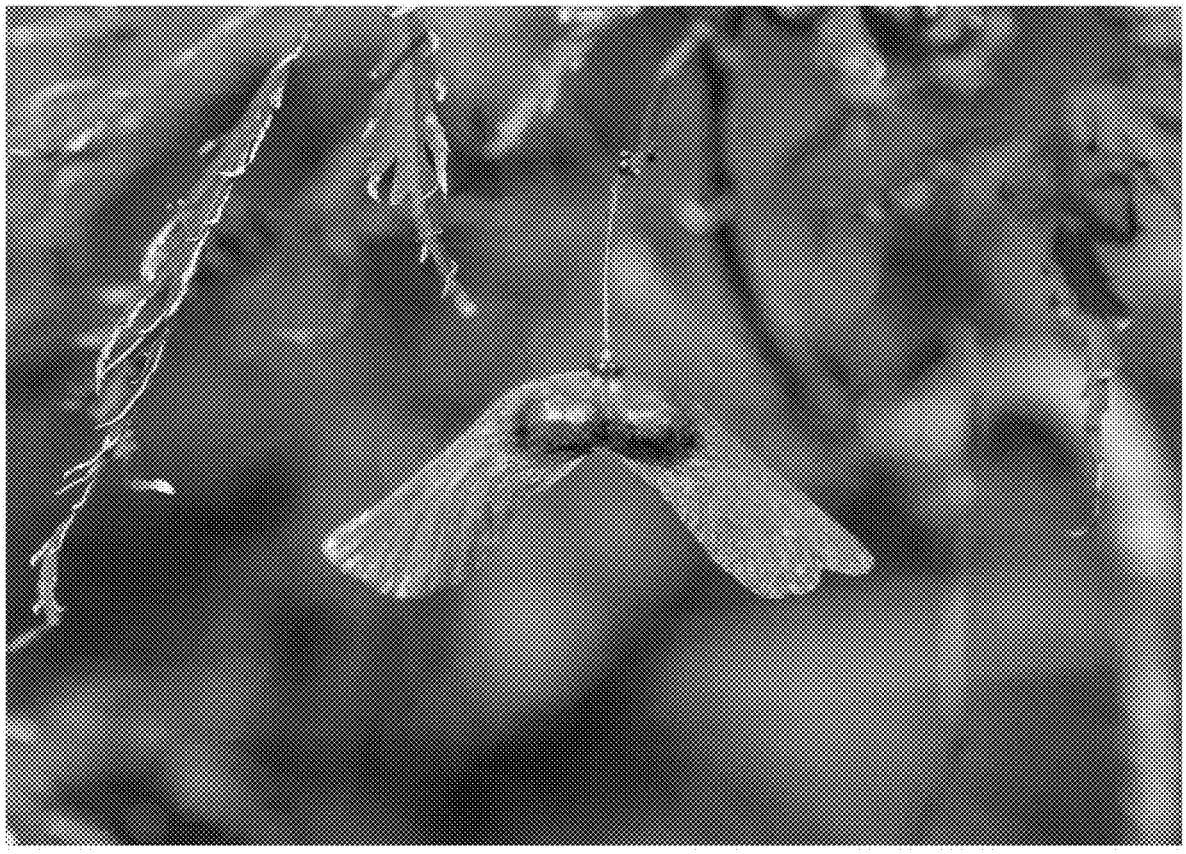
FIG. 5 shows a close-up of an 'INWQ-E92' seed.

The following detailed descriptions set for the distinctive characteristics of 'INWQ-E92'. The data which define these characteristics were collected outdoors in September 2024 on 5-year-old and 12-year-old trees in Boring, Oregon. Color references are to The R.H.S. Colour Chart of The Royal Horticultural Society of London (R.H.S.) Sixth Edition 2015; 2019 reprint, except where general terms of ordinary dictionary significance are used.

Classification:

*Family*.—Sapindaceae.

*Botanical*.—*Acer palmatum*.

*Denomination*.—'INWQ-E92'.

Tree:

*Type*.—Deciduous.

*Shape*.—Mushroom-like habit.

*Growth and branching habit*.—Small, wider than tall garden tree with a spreading, arching and cascading pattern; full-leafed tree.

*Propagation type*.—Vegetative shoots that are grafted onto *Acer palmatum* rootstock (unpatented).

*Height* (*from soil line*).—120 cm at 12 years and 90 cm at 5 years.

*Width* (*horizontal plant diameter*).—150 cm at 12 years and 100 cm at 5 years.

*Growth rate*.—15.0 cm per year.

*Hardiness*.—Hardy from USDA Zones 4 to 8.

*Diameter of the trunk measure at* 10 *cm from the soil line*.—8.5 cm at 12 years and 3.0 cm at 5 years.

*Texture of the bark at* 12 *years*.—*Smooth to very slight texture*.

*Color of the trunk bark*.—Predominantly N155A (Bluish White) and 156A (Yellowish-Grey) in irregular shaped patches arranged over a mixed base colors that include N175A (Moderate Reddish Brown) with less apparent vertical fissures in N165B (Greyed-Orange).

Foliage:

*Arrangement*.—Opposite and simple.

*Quantity of leaves per lateral branch*.—Strong lateral branches 10 or12 leaves occasionally more. Moderate sized lateral branches 6 or 8 leaves Small lower-level lateral branches 2 or 4 leaves

*Shape*.—Palmatilobed; predominantly 5 lobed but also 7 and 9 lobed. The narrow leaf lobes originate at the leaf petiole. First and fifth leaf lobes typically have 1 larger lobe and 2 smaller lobes that may or may not be fully divided with point of origin at the leaf petiole giving the 5 lobed leaf either a 7 or 9 lobed appearance. The leaf lobe width from the petiole attachment to approximately $1/5^{th}$ the length of the leaf lobe is 0.1 cm or the width of the leaf vein and widens slightly 1.0 cm to 1.5 cm at the first and second order leaf veins.

*Apex*.—Narrowly acuminate.

*Base*.—Subcordate.

*Margin*.—Doubly serrate; serrations terminating with a sharp hooked point curved upwards.

*Length*.—7.0 cm to 12.0 cm.

*Width*.—7.0 cm to 12.0 cm.

*Color observation* (*Sep.* 3, 2024).—Immature new leaves: N46A (Strong Red) Mature leaves: N186C (Dark Greyish Red)

*Texture* (*summer leaf*).—Upper surface: Smooth, mid-veins slightly sunken Lower surface: Smooth, mid-veins protruding

*Pubescence*.—Present on new foliage.

*Petiole*.—Length: 2.0 cm to 5.0 cm Diameter: 0.1 cm Color: RHS 46A (Strong Red)

*Leaf bud*.—Color: RHS N145B (Light Yellow-Green) Shape: Conical Height: 0.1 cm

*Venation pattern*.—Main leaf lobe veins located mid-lobe with alternating or paired forward angled lateral veins and smaller inconspicuous reticulate veins.

*Venation color immature leaves*.—RHS 46A (Strong Red).

*Venation color mature leaves*.—RHS 145B (Light Yellow-Green).

Lateral branches/stems:

*Color*.—1-year-old branch: RHS 46A (Strong Red) 2-year-old branch: RHS 153A (Deep Greenish-Yellow)

*Size*.—Upper crown vigorous 1-year-old shoot: 30.0 cm in length and 0.4 cm in width Average 1-year-old shoot: 10.0 cm to 15.0 cm in length and 0.2 cm in width

*Internode length*.—3.0 cm to 5.0 cm; average 8 nodes per vigorous shoot; 4 nodes per average shoot.

*Texture*.—Smooth.

*Lenticels*.—Not visible on most 1-year shoots. Two and three-year-old shoots have small lenticels, generally less than 0.1 cm. No lenticels on trunk. Lenticel color is N155D (Yellowish-White).

Flowers: Observed but ornamentally insignificant.

Fruit/seed: Each paired samara (wing and nut) is 2.0 cm in length and 3.0 cm in width with a rounded to truncate wing tip; the paired or occasionally triplet wings are held at an acute 40-degree angle in small clusters of 1 to 4 samara.

Disease/pest resistance: No pests observed; no specific disease or pest resistance has been observed to date.

COMPARISON WITH PARENTAL AND COMMERCIAL LINES

Table 1 shows a comparison of the differences between 'INWQ-E92' and the female parental variety.

TABLE 1

| Characteristic | 'INWQ-E92' | Female parent |
|---|---|---|
| Hardiness zone | Zone 4-8 | Zone 4-8 |
| Leaf color new | RHS 46A Strong Red | RHS 186C Dark Greyish Red |
| Leaf color mature | RHS 186C Dark Greyish Red | RHS N189A Greyed Green |

TABLE 1-continued

| Characteristic | 'INWQ-E92' | Female parent |
|---|---|---|
| Growth rate | Moderate | Vigorous |
| Branching | Arching, Cascading | Irregular, Spreading |

Table 2 shows a comparison of the differences between 'INWQ-E92' and the commercial Japanese maple 'Tamukeyama' (patent status unknown) and 'Crimson Queen' (patent status unknown).

TABLE 2

| Characteristic | 'INWQ-E92' | Commercial line 'Tamukeyama' | Commercial line 'Crimson Queen' |
|---|---|---|---|
| Hardiness zone | Zone 4-8 | Zone 5-8 | Zone 5-8 |
| Leaf color new | RHS 46A Strong Red | RHS 187A Dark Red | RHS 187A Dark Red |

TABLE 2-continued

| Characteristic | 'INWQ-E92' | Commercial line 'Tamukeyama' | Commercial line 'Crimson Queen' |
|---|---|---|---|
| Leaf color mature | RHS 186C Dark Greyish Red | RHS N199A Moderate Olive Brown | RHS 146A Moderate Olive Green |
| Growth rate | Moderate | Moderate | Slow |
| Branching | Arching, Cascading | Arching, Cascading | Strongly Cascading |

I claim:

1. A new and distinct cultivar of Japanese Maple Tree Named 'INWQ-E92' as illustrated and described herein.

* * * * *